United States Patent [19]

Dolle et al.

[11] Patent Number: 5,585,357

[45] Date of Patent: Dec. 17, 1996

[54] HETEROARYLOXYMETHYL KETONES AS INTERLEUKIN-1β CONVERTING ENZYME INHIBITORS

[75] Inventors: Roland E. Dolle, King of Prussia; Jasbir Singh, Gilbertsville, both of Pa.; David A. Whipple, New London, Conn.; Catherine Prouty, Doylestown, Pa.; Prasad V. Chaturvedula, Cheshire, Conn.; Stanley J. Schmidt, Chester Springs, Pa.; Mohamed M. A. Awad, Westerly, R.I.; Denton W. Hoyer, Exton; Tina M. Ross, Audubon, both of Pa.

[73] Assignee: Sanofi Winthrop Inc., New York, N.Y.

[21] Appl. No.: 593,773

[22] Filed: Jan. 29, 1996

Related U.S. Application Data

[63] Continuation-in-part of Ser. No. 237,920, Apr. 29, 1994, abandoned, which is a continuation-in-part of Ser. No. 71,623, Jun. 3, 1993, abandoned.

[51] Int. Cl.$^6$ .......................... A61K 38/00; A61K 31/415; C07K 5/00; C07D 231/04
[52] U.S. Cl. .................. 514/18; 514/17; 514/19; 514/407; 530/330; 530/332; 548/370.1
[58] Field of Search ................... 514/17, 18, 19, 514/407; 530/330, 332; 548/370.1

[56] References Cited

U.S. PATENT DOCUMENTS 5,055,451  10/1991  Krantz et al. .

FOREIGN PATENT DOCUMENTS

0519748A2  6/1992  European Pat. Off. .
WO91/15577  10/1991  WIPO .

*Primary Examiner*—Michael P. Woodward
*Assistant Examiner*—Benet Prickril
*Attorney, Agent, or Firm*—William J. Davis; Paul E. Dupont

[57] ABSTRACT

Compounds which inhibit interleukin-1β protease activity, pharmaceutical compositions containing the compounds and methods using the compounds are provided. The compounds have the formula

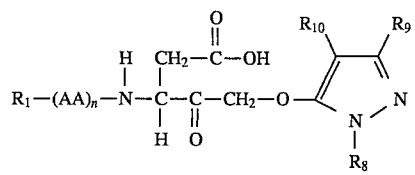

wherein n is 0–2; each AA is independently L-valine or L-alanine; $R_1$ is selected from the group consisting of N-[4-(N,N-dimethylaminomethyl)]benzoyl, N-benzyloxycarbonyl, N-methyl-N-[4-(pyridyl)methyl], N-[4-(pyridyl)methyl]carbonyl, N-3-(piperidinopropionyl), N-[4-(morpholinoethoxy)benzoyl, N-2-(quinuclidinyl)carbonyl, N-(3-pyridyl)methoxy carbonyl, N-(2-pyridyl)methoxy carbonyl, N-methyl-N-benzyl carbonyl, N-methyl-N-[2-(4-pyridyl)ethyl]carbonyl, and N-(N-phenylpiperazino)carbonyl; and $R_8$, $R_9$, $R_{10}$ are each independently hydrogen, lower alkyl, halo substituted methyl, carbalkoxy, benzyl, phenyl, or phenyl mono or disubstituted with fluoro, nitro, methoxy, chloro, trifluoromethyl or methanesulfonyl.

24 Claims, No Drawings

HETEROARYLOXYMETHYL KETONES AS INTERLEUKIN-1β CONVERTING ENZYME INHIBITORS

CROSS REFERENCE TO RELATED APPLICATIONS

This a continuation-in-part of application Ser. No. 08/237,920, filed Apr. 29, 1994, now abandoned, which is a continuation-in-part of application Ser. No. 08/071,623, filed Jun. 3, 1993, now abandoned.

BACKGROUND OF THE INVENTION

1. Field of the Invention

This invention relates to a series of novel amino acid, di- and polypeptide analogs which exhibit selective inhibition of interleukin-1β-converting enzyme, to compositions containing the novel amino acid analogs and methods for therapeutic utility. More particularly, the interleukin-1β-converting enzyme inhibitors described in this invention comprise novel α-substituted methyl ketones which possess particular utility in the treatment of inflammatory and immune-based diseases of lung, central nervous system, and connective tissues.

2. Reported Developments

Interleukin-1β protease (also known as interleukin-1β-converting enzyme or ICE) is the enzyme responsible for processing of the biologically inactive 31 kD precursor IL-1β to the biologically active 17 kD form (Kostura, M. J.; Tocci, M. J.; Limjuco, G.; Chin, J.; Cameron, P.; Hillman, A. G.; Chartrain, N. A.; Schmidt, J. A. *Proc. Nat. Acad. Sci.* 1989, 86, 5227–5231 and Black, R. A.; Kronheim, S. R.; Sleath, P. R. *FEBS Let.*, 1989, 247, 386–391). In addition to acting as one of the body's early responses to injury and infection, IL-1β has also been proposed to act as a mediator of a wide variety of diseases, including rheumatoid arthritis, osteoarthritis, inflammatory bowel disease, sepsis, and acute and chronic myelogenous leukemia (Dinarello, C. A.; Wolff, S. M., *New Engl. J. Med.*, 1993, 328, 106). The naturally occurring IL-1β receptor antagonist has been used to demonstrate the intermediacy of IL-1β in a number of human diseases and animal models (Hannum, C. H.; Wilcox, C. J.; Arend, W. P.; Joslin, G. G.; Dripps, D. J.; Heimdal, P. L.; Armes, L. G.; Sommer, A.; Eisenberg, S. P.; Thompson, R. C., *Nature*, 1990, 343, 336–340; Eisenberg, S. P.; Evans, R. J.; Arend, W. P.; Verderber, E.; Brewer, M. T.; Hannum, C. H.; Thompson, R. C., *Nature* 1990, 343, 341–346; Ohlsson, K.; Bjork, P.; Bergenfeldt, M.; Hageman, R.; Thompson, R. C., *Nature.*, 1990, 348, 550–552; and Wakabayashi, G., *GASEB*, 1991, 338–343). The specific role of IL-1β in inflammation and immunomodulation is supported by the recent observation that the cowpox virus employs an inhibitor of ICE to suppress the inflammatory response of its host (Ray, C. A. et al, *Cell*, 1992, 69, 597–604).

The utility of ICE inhibitors in modifying certain IL-1β mediated disease states has been suggested and demonstrated in vivo by several workers in the field. The following review of the current state of the art in ICE research further supports such utility of ICE inhibitors:

1) WO 9309135, published 11 May 1993, teaches that peptide-based aspartic acid arylacyloxy-and aryoxymethyl ketones are potent inhibitors of ICE in vitro. These compounds also specifically inhibited ICE in the whole cell (in vivo) by their ability to inhibit the formation of mature IL-1β in whole cells. These ICE inhibitors also demonstrated utility in reducing fever and inflammation/swelling in rats.

2) Patients with Lyme disease sometimes develop Lyme arthritis. B. burgdorferi, the causative agent of Lyme disease, is a potent inducer of IL-1β synthesis by mononuclear cells. Miller et al. (Miller, L. C.; Lynch, E. A. Isa, S.; Logan, J. W.; Dinarello, C. A.; and Steere, A. C., "Balance of synovial fluid IL-1β and IL-1β Receptor Antagonist and Recovery from Lyme arthritis", *Lancet* (1993) 341; 146–148) showed that in patients who recovered quickly from Lyme Arthritis, the balance in synovial fluid of IL-1-beta and IL-1ra was in favor of IL-ra. When the balance was shifted in favor of IL-1β, it took significantly longer for the disease to resolve. The conclusion was that the excess IL-1ra blocked the effects of the IL-1β in the patients studied.

3) IL-1 is present in affected tissues in ulcerative colitis in humans. In animal models of the disease, IL-1β levels correlate with disease severity. In the model, administration of 1L-1ra reduced tissue necrosis and the number of inflammatory cells in the colon. See, Cominelli, F.; Nast, C. C.; Clark, B. D.; Schindler, R., Llerena, R.; Eysselein, V. E.; Thompson, R. C.; and Dinarello, C. A.; "Interleukin-1 Gene Expression, Synthesis, and Effect of Specific IL-1 Receptor Blockade in Rabbit Immune Complex Colitis" *J. Clin. Investigations* (1990) Vol. 86, pp, 972–980.

4) IL-1ra supresses joint swelling in the PG-APS model of arthritis in rats. See Schwab, J. H.; Anderie, S. K.; Brown, R. R.; Dalldorf, F. G. and Thompson, R. C., "Pro- and Anti-Inflammatory Roles of Interelukin-1 in Recurrence of Bacterial Cell Wall-Induced Arthritis in Rats". *Infect. Immun.* (1991) 59; 4436–4442.

5) IL-1ra shows efficacy in an small open-label human Rheumatoid Arthritis trial. See, Lebsack, M. E.; Paul, C. C.; Bloedow, C. C.; Burch, F. X.; Sack, M. A.; Chase, W., and Catalano, M. A. "Subcutaneous IL-1 Receptor Antagonist in Patients with Rheumatoid Arthritis", *Arth. Rheum.* (1991) 34; 545.

6) IL-1 appears to be an autocrine growth factor for the proliferation of chronic myelogenous leukemia cells. Both IL-1ra and sIL-1R inhibit colony growth in cells removed from leukemia patients. See, Estrov, Z.; Kurzrock, R.; Wetzler, M.; Kantarjian, H.; Blake, M.; Harris, D.; Gutterman, J. U.; and Talpaz, M., "Supression of Chronic Myelogenous Leukemia Colony Growth by Interleukin-1 (IL-1) Receptor Antagonist and Soluble IL-1 Receptors: a Novel Application for Inhibitors of IL-1 Activity". *Blood* (1991) 78; 1476–1484.

7) IL-1 was also found to be a potent bone resorptive agent capable, upon infusion into mice, of causing hypercalcemia and increase in bone resorptive surface. See, Sabatini, M. et al., PNAS 85:5235–5239, 1988.

8) Reduction of inflammation and pyrexia was found in the rat by oral administration of SDZ 224–015, an inhibitor of the IL-1β converting enzyme by Elford et al., Br. J. Pharmacol (England), June 1995, 115(4) p. 601–6.

The present invention also relates to the modulation of processing of IL-1β for the treatment of rheumatoid arthritis. Levels of IL-1β are known to be elevated in the synovial fluid of patients with the disease. Additionally, IL-1β stimulates the synthesis of enzymes believed to be involved in inflammation, such as collagenase and $PLA_2$, and produces joint destruction which is very similar to rheumatoid arthritis following intra-articular injection in animals.

A limited number of peptidyl methyl ketone analogs constitute a well-known class of compounds having Cysteine protease (papain, cathepsin B) inhibitory activity. These peptidyl methyl ketone analogs have been reviewed by D. Rich in Chapter 4 of "Proteinase Inhibitors", Barrett, A. J. and Salvensen, G., eds., Elsevier, 1986. More recently, a-aryloxy and a-arylacyloxy methyl ketones have also been described as inhibitors of cysteine protease (Krantz, A. et al, Biochemistry, 30, p. 4678–4687, 1991).

These peptide analogs, however, are essentially devoid of potency and selectivity in inhibiting ICE.

An effective therapy has yet to be developed for the treatment of IL-1β mediated inflammatory diseases. Consequently, there is a need for therapeutic agents effective in the treatment and prevention of these diseases.

SUMMARY OF THE INVENTION

According to the present invention, there is provided a compound of the formula (I) and a pharmaceutically acceptable salt thereof:

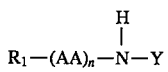
(I)

wherein:

n is 0–4;

Y is

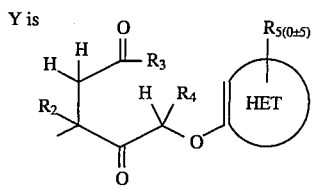

and when $R_3$ is OH, then Y can also be

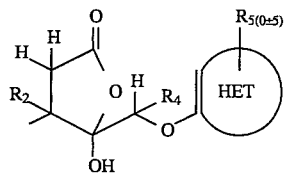

$R_2$ is H or deuterium;

$R_3$ is OH, $OR_6$, $NR_6OR_7$ or $NR_6R_7$, where $R_6$ and $R_7$ are independently H, alkyl, aralkyl, heteroaralkyl, aryl or heteroaryl;

$R_4$ is H or alkyl;

$R_5$ is H, alkyl, alkenyl, aryl, heteroaryl, aralkyl, heteroaralkyl, aralkenyl, heteroaralkenyl, hydroxy, alkoxy, 2-(alkyoxy)ethoxy, 2-(alkyoxy)aminoethyl and 2-(alkyoxy)-N-alkylaminoethyl, aralkoxy, heteroaralkoxy, alkylacyloxy, aralkylacyloxy, heteroaralkylacyloxy aracyloxy, heteroaracyloxy, aryloxyalkylacyloxy heteroaryloxyalkylacyloxy, alkylacyl, aralkylacyl, heteroaralkylacyl alkylacylamino, aralkylacylamino, heteroaralkylacylamino, aracylamino heteroaracylamino, aryloxyalkylacylamino, heteroaryloxyalkylacylamino alkyloxyalkylacylamino, alkoxyacylamino, aralkoxyacylamino heteroaralkoxyacylamino, aracyl, heteroaracyl, aryloxyalkylacyl heteroaryloxyalkylacyl, halo, haloalkyl, guanidino, mono- and di-alkylguanidino, mono- and di-aralkylguanidino, mono- and di-heteroaralkylguanidino, alkylacylguanidino, aralkyla- cylguanidino, heteroaralkylguanidino, aracylguanidino, heteroarylguanidino, amidino, mono- and di-alkylamidino, mono- and diaralkylamidino, mono- and di-heteroaralkylamidino, amino, mono- and dialkylamino, mono- and di-aralkylamino, mono- and di-heteroaralkylamino, carboxy, alkylcarboxy, carbalkoxy, carbalalkoxy, carbheteroaralkoxy, carbalkoxyalkenyl, carboxamido, mono- and dialkylcarboxamido, mono- and diarcarboxamido, mono and di-heteroarcarboxamido, mono- and di-aralkylcarboxamido, mono- and di-heteroaralkylcarboxamido, thio, alkylthio, arylthio, heteroarylthio, aralkylthio, heteroaralkylthio, sulfonamido, mono- and di-alkylsulfonamido, mono- and di-aralkylsulfonamido, mono- and di-heteroaralkylsulfonamido, morpholinosulfonamido, alkylsulfonyl, aralkylsulfonyl, heteroaralkylsulfonyl, arylsulfonyl, heteroarylsulfonyl, nitro, cyano, N-morpholinoalkyl, N-morpholinoalkoxy, N-morpholinoaralkyl, N-morpholinoaralkoxy, N-morpholinoheteroaralkyl, N-morpholinoheteroaralkoxy, N-mono and N,N-dialkylaminoalkyl and N-mono- and N,N-dialkylaminoethoxy, quinuclidinylamino, quinuclidinyloxy, quinuclidinocarbonyl or ureido; HET is a heteroaryl;

AA is independently selected from the group consisting of (a) and (b) where group (a) is defined as an amino acid of formula II:

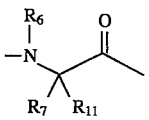
(II)

where $R_6$ and $R_7$ are defined as above and $R_{11}$ is $(CR_6R_7)_{0-6}$—$R_{12}$ where $R_{12}$ is designated as either an aryl, heteroaryl or a radical optionally selected from $R_5$ wherein $R_5$, $R_6$, $R_7$ are defined previously;

and group (b) is selected from the group consisting of:

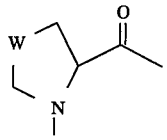
(1)

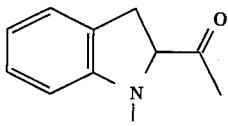
(2)

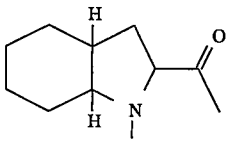
(3)

(4)

-continued

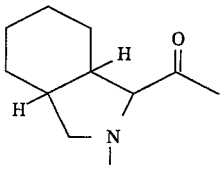
(5)

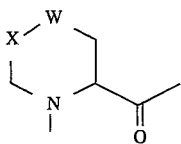
(6)

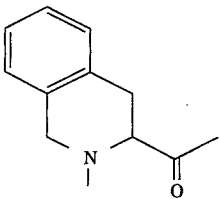
(7)

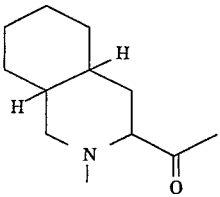
(9)

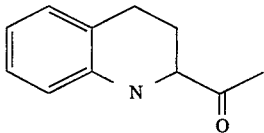
(9)

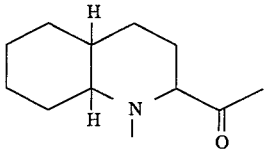
(10)

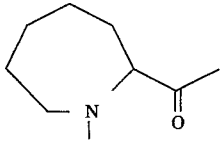
(11)

and

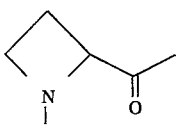
(12)

and

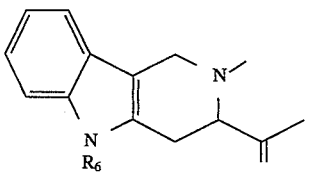
(13)

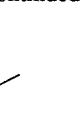
(14)

where W and X are optionally $CH_2$, O, S, or $NR_{61}$; and $R_1$ is $R_{12}$—CO— or $R_{12}SO_2$—, where $R_{12}$ is as previously defined.

Heteroaryl is defined as an unsubstituted or an optionally substituted mono- or bicyclic ring system of about 5 to about 12 carbon atoms and where each monocyclic ring may possess from 0 to about 4 heteroatoms, and each bicyclic ring may possess about 0 to about 5 heteroatoms selected from N, O, and S provided said heteroatoms are not vicinal oxygen and/or sulfur atoms and were the substituents, numbering from 0 to about 5 may be located at any appropriate position of the ring system and are described by $R_5$.

Examples of such mono- and bicyclic ring systems which are by no means meant to limit the scope of this invention, include benzofuran, benzothiophene, indole, benzopyrazole, coumarin, isoquinoline, pyrrole, thiophene, furan, thiazole, imidazole, pyrazole, triazole, quinoline, pyrollidenone, pyrimidine, pyridine, pyridone, pyrazine, pyridazine, isothiazole, isoxazole and tetrazole.

A preferred embodiment of this invention is where HET is the pyrazole of formula III:

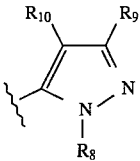
(III)

wherein $R_8$, $R_9$ and $R_{10}$ are independently aryl, heteroaryl, or a radical optionally selected from $R_5$; and where $R_9$ and $R_{10}$ taken together may be aryl, heteroaryl, cyclopentyl, cyclohexyl, cycloheptyl or cyclooctyl.

As used herein, the term pharmaceutically acceptable salts include the acid and base addition salts.

The term acid addition salts refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline and caffeine.

As employed above and throughout the disclosure, the following terms, unless otherwise indicated, shall be understood to have the following meanings:

"Alkyl" is defined as a saturated aliphatic hydrocarbon which may be either straight- or branched-chain or cyclic. Preferred groups have no more than about 12 carbon atoms and may be methyl, ethyl and structural isomers of propyl, butyl, pentyl, hexyl, heptyl, octyl, nonyl, decyl, undecyl, dodecyl, cyclopropyl, cyclobutyl, cyclopentyl, cyclohexyl, cycloheptyl and cyclooctyl.

"Aryl" is defined as a phenyl or naphthyl or a substituted phenyl and a substituted naphthyl ring wherein one or more of the hydrogens has been replaced by the same or different substituents as selected from $R_5$.

"Alkoxy" refers to an alkyl-O-group. For example, methoxy or ethoxy.

"Aryloxy" refers to an aryl-O-group. For example, phenoxy.

"Heteroxy" refers to a hetero-O-group. For example, 4-pyridyloxy.

"Aralkyl" refers to an alkyl group substituted by an aryl radical. For example, benzyl.

"Heteroaralkyl" refers to an alkyl group substituted by a heteroaryl radical. For example, (4-pyridyl)methyl.

"Alkenyl" is defined as an unsaturated aliphatic hydrocarbon which may be either straight- or branched-chain of cyclic. Preferred groups have no more than about 12 carbon atoms and no fewer than 2 carbon atoms and contain from one to up to about 6 double bonds. Examples of alkenyl groups include ethenyl, propenyl, 1-hexenyl, 1-3-hexdienyl, 2-methyl-2-butenyl, 2-methyl-3-pentenyl, cyclopentenyl, cyclohexenyl and cyclobutenyl.

"Alkylacyl" refers to an alkyl-C(O)-group. For example, acetyl or propionyl.

"Alkylacyloxy" refers to an alkyl-C(O)O-group. For example, an acetoxy group.

"Alkylacylamino" means alkyl-C(O)—$NR_7$ where $R_7$ has been defined previously.

"Alkylacylguanidino" means alkyl-C(O)$NR_6$C($NR_7$)NH— where $R_6$ and $R_7$ have been defined previously.

"Ureido" refers to an $R_6R_7$N—C(O)—N—$R_6$-group where $R_6$ and $R_7$ are described previously.

"Haloalkyl" is defined as a saturated aliphatic hydrocarbon of 1–12 carbon atoms which may be either straight- or branched-chain or cyclic and where one or more of the hydrogen atoms is replaced with halogen. Preferred haloalkyl groups include trifluoromethyl and pentafluoroethyl.

"Halo" means bromo, chloro and fluoro.

The present invention also concerns the pharmaceutical composition and method of treatment of IL-1β protease mediated disease states or disorders in a mammal in need of such treatment comprising the administration of IL-1β protease inhibitors of formula (I) as the active agent. These disease states and disorders include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, immune-based diseases, such as hypersensitivity; auto-immune diseases, such as multiple sclerosis; bone diseases; and certain tumors.

In the practice of this invention an effective amount of a compound of the invention or a pharmaceutical composition thereof is administered to the subject in need of, or desiring, such treatment. These compounds or compositions may be administered by any of a variety of routes depending upon the specific end use, including orally, parenterally (including subcutaneous, intraarticular, intramuscular and intravenous administration), rectally, buccally (including sublingually), transdermally or intranasally. The most suitable route in any given case will depend upon the use, the particular active ingredient, and the subject involved. The compound or composition may also be administered by means of controlled-release, depot implant or injectable formulations as described more fully herein.

In general, for the uses as described in the instant invention, it is expedient to administer the active ingredient in amounts between about 0.1 and 100 mg/kg body weight, most preferably from about 0.1 to 30 mg/kg body weight for human therapy, the active ingredient will be administered preferably in the range of from about 0.1 to about 20–b 50 mg/kg/day. This administration may be accomplished by a single administration, by distribution over several applications or by slow release in order to achieve the most effective results. When administered as a single dose, administration will most preferably be in the range of from about 0.1 to mg/kg to about 10 mg/kg.

The exact dose and regimen for administration of these compounds and compositions will necessarily be dependent upon the needs of the individual subject being treated, the type of treatment, and the degree of affliction or need. In general, parenteral administration requires lower dosage than other methods of administration which are more dependent upon absorption.

A further aspect of the present invention relates to pharmaceutical compositions comprising as an active ingredient a compound of the present invention in a mixture with a pharmaceutically acceptable, non-toxic carrier. As mentioned above, such compositions may be prepared for use for parenteral (subcutaneous, intraarticular, intramuscular or intravenous) administration, particularly in the form of liquid solutions or suspensions; for oral or buccal administration, particularly in the form of tablets or capsules; or intranasally, particularly in the form of powders, nasal drops or aerosols.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

When administered orally (or rectally) the compounds will usually be formulated into a unit dosage form such as a tablet, capsule, suppository or cachet. Such formulations typically include a solid, semi-solid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, aginates, tragacanth, gelatin, syrup, methylcellulose, polyoxyethylene sorbitar monolaurate, methyl hydroxybenzoate, propyl hydroxybenzoate, talc, and magnesium stearate.

The compositions may be prepared by any of the methods well-known in the pharmaceutical art, for example as described in *Remington's Pharmaceutical Sciences,* 17th edition, Mack Publishing Company, Easton, Pa., 1985. Formulations for parenteral administration may contain as common excipients sterile water or saline, alkylene glycols such as propylene glycol, polyalkylene glycols such as polyethylene glycol, oils of vegetable origin, hydrogenated naphthalenes and the like. Examples of vehicles for parenteral administration include water, aqueous vehicles such as saline, Ringer's solution, dextrose solution, and Hank's solution and nonaqueous vehicles such as fixed oils (such as corn, cottonseed, peanut, and sesame), ethyl oleate, and isopropyl myristate. Sterile saline is a preferred vehicle and the compounds are sufficiently water soluble to be made up as a solution for all foreseeable needs. The vehicle may contain minor amounts of additives such as substances that enhance solubility, isotonicity, and chemical stability, e.g., antioxidants, buffers, and preservatives. For oral administration, the formula can be enhanced by the addition of bile salts and also by the addition of acylcarnitines (*Am. J. Physiol.* 251:332 (1986)). Formulations for nasal administration may be solid and contain as excipients, for example, lactose or dextran, or may be aqueous or oily solutions for administration in the form of nasal drops or metered spray. For buccal administration typical excipients include sugars, calcium stearate, magnesium stearate, pregelatinated starch, and the like.

When formulated for nasal administration the absorption across the nasal mucous membrane is enhanced by surfactant acids, such as for example, glycocholic acid, cholic acid, taurocholic acid, ethocholic acid, desoxycholic acid, chenodesoxycholic acid, dehydrocholic acid, glycodeoxycholic acid, and the like (See, B. H. Vickery, "LHRH and its Analogs-Contraception and Therapeutic Applications", Pt. 2, B. H. Vickery and J. S. Nester, Eds., MTP Press, Lancaster, UK, 1987).

DETAILED DESCRIPTION OF THE INVENTION

The compounds of this invention are prepared by one of two related general synthetic methods as described in Schemes 1 and 2. Referring to Scheme I, the first step of the method involves the synthesis of Z-protected amino acid bromomethyl ketones (formula 2), where the "Z-group" refers to the "benzyloxycarbonyl group". Methods for the preparation of various Z-protected aspartic acids and aspartic acid-containing peptides (formula 1) which are used as the starting materials for the synthesis of bromomethyl ketones (formula 2) are well established in the art. (See, for example, "The Peptides", E. Gross and J. Meienhofer, Eds. Academic Press, Orlando, Fla., Vol. 1–3, 1979.) The Z-protected amino acids, dipeptides, and polypeptides (formula 1), which in some cases are commercially available, are then converted to the aspartic acid-containing bromoketones (formula 2) by way of hydrobromination of a diazomethyl ketone intermediate. This is accomplished by methods described in Shaw, E. and Ruscica, J.; *J. Biol. Chem.*, 1968, 243, 6312 and Green, E. D. J. and Shaw, E.; *J. Biol. Chem.*, 1981, 256, 1923.

The t-butyl ester bromoketone (formula 2) is reacted with a variety of pyrazolones. This is conducted by exposing the bromomethyl ketone to an excess of the pyrazolone in a DMF containing sodium or potassium hydride or potassium fluoride. The reaction can be conveniently monitored by thin layer chromatography (TLC) and once the TLC indicates that the displacement of the bromide with the pyrazolone is completed, the product is isolated using standard procedures. The desired aspartic acid-pyrazolylmethyl ketone mono-t-butyl ester (formula 3) may be purified by conventional met recrystallization and silica gel column chromatography.

SCHEME 1

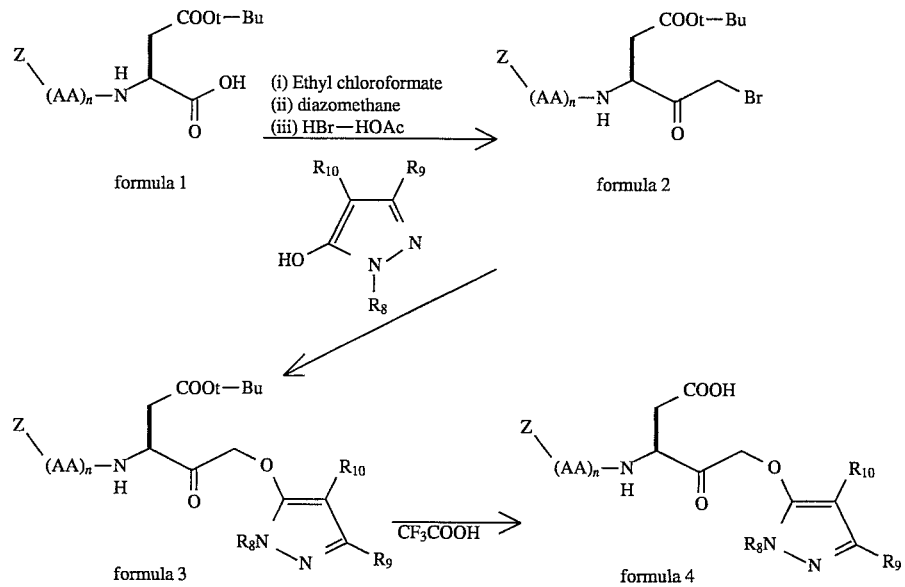

SCHEME 2

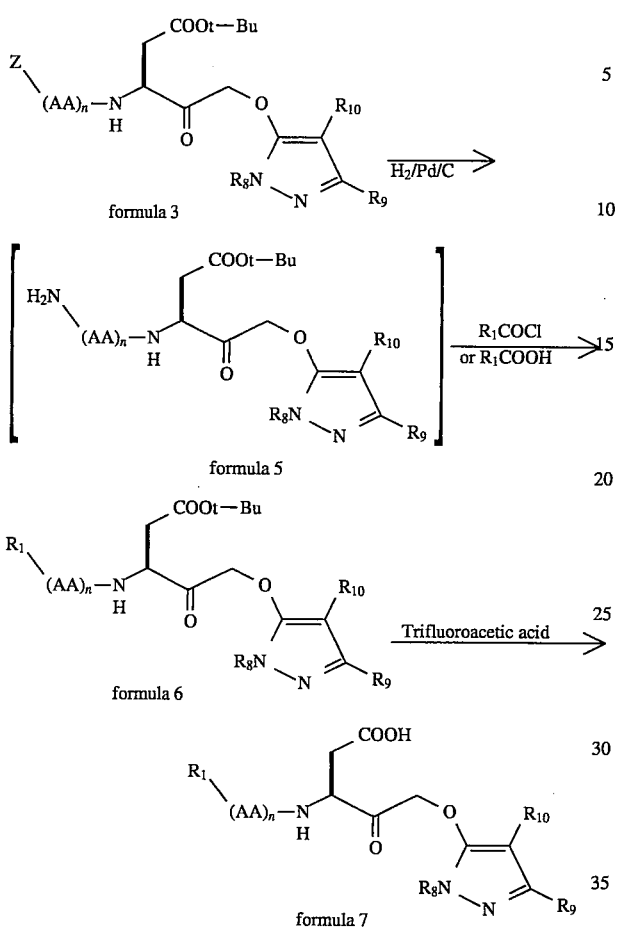

formula 3
formula 5
formula 6
formula 7 wherein

AA, $R_1$, $R_8$, $R_9$, $R_{10}$ and n are as defined in formula (I) and Z is defined as the benzyloxycarbonyl group.

The remaining synthetic transformation to generate the ICE inhibitors is hydrolysis of the t-butyl ester function. This is conducted by exposing the ester to a 25% solution of trifluoroacetic acid in methyl chloride at 25° C. The de-esterification is usually complete within 3 h and the removal of the volatile TFA and solvent affords the aspartic acid derivative (formula 4). The yield of the reaction is quantitative in most instances, providing the t-butyl ester starting material is of high purity. Purification, if required, can be performed by recrystallization or chromatographic techniques which are well known to those skilled in the art. A solution of 3 molar anhydrous HCl in ethyl acetate may be used in place of TFA-methylene chloride solution with equal efficiency.

In scheme 2, the synthesis of pyrazolyloxymethyl ketones, which possess an N-terminal group, other than the Z- group are described. The aspartic acid derivatives of formula 3 are the starting material for the synthesis of these compounds. The Z-group is removed to generate an N-terminal amine (formula 5) under hydrogenolytic conditions. The reagents and conditions used to carry out the hydrogenation reaction are hydrogen gas, ambient temperature and pressure, 5%-Pd/C as the catalyst in an alcoholic solvent (ethanol), optionally containing 2 equivalents of hydrochloric acid.

The N-terminal amine is then condensed with carboxylic acid chloride or a mixed anhydride (The Practice of Peptide Synthesis: M Bodanszky, Springer-Verlag, New York, 1984) to yield an iamide (formula 6). Lastly, the t-butyl ester is removed with trifluoroacetic acid to afford the aspartic acid derivative (formula 7).

Compounds of formulas 4 and 7 may exist as a cyclic hemiketal (where the carboxylate oxygen adds intramolecularly to the ketone carbonyl) and such structures are considered within the scope of this invention.

The pyrazolones used in the reaction with the bromomethyl ketones can be either purchased from commercial sources or synthesized by adopting known procedures including those described in (1) Hansel, W., *Justus Liebigs Ann. Chem.*, 1976, 1380–1394; (2) Knorr, L., *Justus Liebigs Ann, Chem.*, 1987, 238, 137; (3) Watanabe, Y. et al, *Chem. Pharm. Bull.* (Japan), 1990, 38, 2726; (4) Grillot, G. F. et al, *J. Org. Chem.*, 1958, 23, 119. Their synthesis is readily deduced by those skilled in the art of organic synthesis.

The following examples will further illustrate the compounds of the present invention.

EXAMPLE 1

N-[4-(N,N-Dimethylaminomethyl)]benzoyl-L-valine-L-aspartic acid 5-(1-phenyl-3-trifluoromethyl)pyrazoyloxymethly ketone Part A:

N-Benzyloxycarbonyl-L-valine-L-aspartic acid bromomethyl ketone β-tert butyl ester (1.16 mmol) was dissolved in 2 mL of DMF containing 1-phenyl-3-trifluoromethyl-5-pyrazolone (1.4 mmol) and powdered anhydrous KF (1.6 mmol). The reaction mixture was stirred under $N_2$ for 16. hrs. The mixture was diluted with water (30 mL), extracted with ether (3×20 mL), and the organic layer was washed with 0.1N NaOH (3×10 mL) followed by brine. The ether solution was dried over magnesium sulfate and concentrated in vacuo to afford (85%) of the β-tert-butyl ester (formula 3) as a brown solid.

Part B:

N-Benzyloxycarbonyl-L-valine-L-aspartic acid 5-(1-phenyl-3-trifluoromethyl)pyrazoyloxymethyl ketone β-tert-butyl ester (2 mmol; Part A above) was dissolved in absolute ethanol (100 mL) containing 2 equiv. of 6N aqueous HCl (4 mmol) and 10% palladium on carbon. The reaction mixture was stirred under an ambient atmosphere of $H_2$ gas for about 1 hr. The solution was filtered and the solvent was removed in vacuo to give the corresponding HCl-salt (formula 6) which was used immediately in the subsequent reaction.

Part C:

The HCl-salt obtained in Part B above was dissolved in $CH_2Cl_2$ (10 mL), cooled to −20° C. and N-[4-(N,N-dimethylaminomethyl)]benzoyl chloride (4 mmol) was added followed by the addition of 10 mg of dimethylamino pyridine (DMAP) and N-methylmorpholine (5 mmol). The reaction mixture was stirred for 2 hrs at 25° C. The solvent was removed in vacuo and the residue was dissolved in EtOAc (10 mL) which was then washed with water, 0.01N aqueous HCl, saturated $NaHCO_3$, brine and dried over $MgSO_4$. The EtOAC was removed in vacuo and the residue was chromatographed on silica gel ($CH_2Cl_2$-MeOH) to obtain N-(4-(N,N-dmethylaminomethyl)benzoyl-L-valine-L-aspartic acid (5-(1-phenyl-3-trifluoromethyl)pyrazoyloxymethyl ketone p-tert-butyl ester (formula 7)in 50% yield.

Part D:

The β-tert-butyl ester obtained in Part C above (1 mmol) was dissolved in 25% trifluoroacetic acid –75% $CH_2Cl_2$ and the solution was stirred for 2 hrs at 25° C. The solvent was removed in vacuo and the residue was triturated with ether. The white solid was collected and dried to give the title compound in 100% yield. Mass spectrum: m/z 618 (M+H).

The 4-(N,N-dimethylaminomethyl)benzoyl chloride was prepared by reacting the acid with excess oxalyl chloride for 1 hr at 25° C. The 4-(N,N-dimethylaminomethyl)benzoic acid was in turn prepared from methyl 4-aminomethylbenzoate via reductive alkylation ($CH_2O$, $Na(OAc)_3BH$ as in *J. Org. Chem.*, 1972, 37, 1673) followed by hydrolysis using 10% aqueous NaOH.

Following the procedure described in Schemes 1 and 2 and by analogy with Example 1, the following compounds were prepared.

EXAMPLE 2

N-Benzyloxycarbonyl-L-aspartic acid 5-(1,3-dimethyl)pyrazolyoxymethl ketone

Mass spectrum: m/z=376 (M+H)

EXAMPLE 3

N-Benzyloxycarbonyl-L-aspartic acid 5-(1-phenyl-3-trifluoromethyl)pyrazolyloxy methyl ketone Mass spectrum: m/z=492 (M+H)

EXAMPLE 4

N-Benzyloxycarbonyl-L-aspartic acid 5-(1-(p-fluorophenyl)-3-methyl)pyrazolyloxymethyl ketone Mass spectrum: m/z=456 (M+H)

EXAMPLE 5

N-Benzyloxycarbonyl-L-aspartic acid 5-(1-(p-nitrophenyl)-3-methyl)pyrazolyloxymethyl ketone Anal. Calcd. for $C_{23}H_{22}N_4O_8 \cdot CF_3CO_2H$: C, 50.34; H, 3.89; N, 9.39. Found: C, 50.48; H, 4.02; N, 9.33

EXAMPLE 6

N-Benzyloxycarbonyl-L-aspartic acid 5-(1-(p-methoxyphenyl)-3-methyl)pyrazolyloxymethyl ketone Anal. Calcd. for $C_{24}H_{25}N_3O_7 \cdot 1.25\ C_3CO_2H$: C, 52.18; H, 4.34; N, 6.89. Found: C, 51.94; H, 4.30; N, 6.71

EXAMPLE 7

N-Benzyloxycarbonyl-L-aspartic acid 5-(1-(p-chlorphenyl)-3-methyl)pyrazolyloxymethyl ketone Mass spectrum: m/z=472 (M+H)

EXAMPLE 8

N-Benzyloxycarbonyl-L-valine-L-alanine-L-aspartic acid 5-(1-phenyl-3-methyl)pyrozolyoxmethyl ketone Mass spectrum: m/z=608 (M+H)

EXAMPLE 9

N-Benzyloxycarbonyl-L-aspartic acid 5-(1-phenyl-3-methyl)pyrozolyloxymethyl ketone Mass spectrum: m/z=438 (M+H)

EXAMPLE 10

N-Benzyloxycarbonyl-L-aspartic acid 5-(1-(m-chlorophenyl)-3-methyl pyrazolyloxymethyl ketone Anal. Calcd. for $C_{23}H_{22}ClN_3O_6 \cdot 0.9\ CF_3CO_2H$: C, 51.85; H, 4.02; N, 7.31. Found: C, 52.08; H, 4.24; N, 6.98

EXAMPLE 11

N-Benzyloxycarbonyl-L-aspartic acid 5-(1-benzyl-3-trifluoromethyl)pyrazolyloxy methyl ketone Mass spectrum: m/z=506 (M+H)

EXAMPLE 12

N-Benzyloxycarbonyl-L-valine-L-alanine-L-aspartic acid 5-(1-phenyl-3-trifluoromethyl)pyrazolyloxy ketone Mass spectrum: m/z=662 (M+H)

EXAMPLE 13

N-Benzyloxycarbonyl-L-aspartic acid 5-(1-(m,p-dichlorophenyl)- 3-methyl)pyrazolyloxymethyl ketone Mass spectrum: m/z=560 (M+)

EXAMPLE 14

N-Benzyloxycarbonyl-L-valine-L-aspartic acid 5-(1-phenyl-3-trifluoromethyl) pyrazolyloxymethyl ketone Mass spectrum: m/z=591 (M+H)

EXAMPLE 15

N-Benzyloxycarbonyl-L-valine-L-aspartic acid 5-(1-phenyl-3-methyl)pyrazolyloxymethyl ketone Mass spectrum: m/z=537 (M+H)

EXAMPLE 16

N-Benzyloxycarbonyl-L-valine-L-aspartic acid 5-(1-phenyl-3-t-butyl)pyrazolyloxymethyl ketone Anal. Calcd. for $C_{31}H_{38}N_4O_7 \cdot CF_3CO_2H \cdot 1.5\ H_2O$: C, 55.07; H, 5.88; N, 7.78. Found: C, 55.13; H, 5.48; N, 7.54

EXAMPLE 17

N-Benzyloxycarbonyl-L-valine-L-aspartic acid 5-(1-(p-trifluoroemethylphenyl)-3-methyl) pyrazolyloxymethyl ketone Mass spectrum: m/z=605 (M+H)

EXAMPLE 18

N-Benzyloxycarbonyl-L-aspartic acid 5-(1-(p-methanesulfonylphenyl)-3-trifluoromethyl) pyrazolyloxymethyl ketone Mass spectrum: m/z=570 (M+H)

EXAMPLE 19

N-4-(N,N-Dimethylaminomethyl)benzoyl- L-valine-L-alanine-L-aspartic acid 5-(1-phenyl-3-trifluoromethyl)pyrazolyloxymethyl ketone m.p. 82°–84° C.

EXAMPLE 20

N-Benzyloxycarbonyl-L-aspartic acid 5-(1,3-dimethyl-4-phenyl)pyrazolyloxymethyl ketone Anal. Calcd. for $C_{24}H_{25}N_3O_6 \cdot 1.25\ CF_2CO_2H$; C, 53.58; H, 4.45; N, 7.07. Found: C, 53.57; H, 4.57; N, 6.85

EXAMPLE 21

N-Benzyloxycarbonyl-L-valine-L-aspartic acid 5-(1-(p-methanesulfonylphenyl)-3-methyl) pyrazolyloxymethyl ketone Mass spectrum: m/z=615 (M+H)

EXAMPLE 22

N-Benzyloxycarbonyl-L-valine-L-aspartic acid 5-(1,3-dimethyl-4-phenyl)pyrazolyloxymethyl ketone Mass spectrum: m/z=551 (M+H)

EXAMPLE 23

N-Benzyloxycarbonyl-L-valine-L-aspartic acid 5-(1-phenyl-3-carbethoxy)pyrazolyloxymethyl ketone Mass spectrum: m/z=595 (M+H)

EXAMPLE 24

N-Benzyloxycarbonyl-L-valine-L-aspartic acid 5-(1,3-diphenyl)pyrazolyloxy-methyl ketone Mass spectrum: m/z=599 (M+H)

EXAMPLE 25

N-Methyl-N-4-[pyridyl)methyl]carbamoyl-valine-L-alanine-L-aspartic acid 5-(1-phenyl-3-trifluoromethyl)pyrazolyloxymethyl ketone Mass spectrum: m/z=676 (M+H)

EXAMPLE 26

N-[4-(pyridyl)methyl]carbamoyl-L-valine- L-alanine-L-aspartic acid 5-(1-phenyl-3-trifluoromethyl)pyrazolyloxymethyl ketone Mass spectrum: m/z=662 (M+H)

EXAMPLE 27

N-Benzyloxycarbonyl-L-valine-L-alanine-D-aspartic acid 5-(1-phenyl-3-trifluoromethyl)pyrazolyloxymethyl ketone Mass spectrum: m/z=608 (M+H)

EXAMPLE 28

N-Benzyloxycarbonyl-L-valine-L-aspartic acid 5-(1-(p-chlorophenyl)-3-methyl-4-phenyl) pyrazolyloxymethyl ketone Anal. Calcd. for $C_{34}H_{35}ClN_4O_7 \cdot 0.7\ CF_3CO_2H$: C, 58.49; H, 4.95; N, 7.71. Found: C, 58.68; H, 5.15; N, 7.34

EXAMPLE 29

N-Benzyloxycarbonyl-L-valine-L-aspartic acid 5-(1,4-diphenyl-3-methyl)pyrazolyloxymethyl ketone Mass spectrum: m/z=613 (M+H)

EXAMPLE 30

N-3-(piperidinopropionyl)-L-valine-L-alanine- L-aspartic acid 5-(1-phenyl-3-methyl)pyrazolyloxymethyl ketone Mass spectrum: m/z=667 (M+H)

EXAMPLE 31

N-[4-(morpholinoethoxy)benzoyl]-L-valine- L-alanine-L-aspartic acid 5-(1-phenyl-3-trifluoromethyl)pyrazolyloxymethyl ketone Mass spectrum: m/z=761 (M+H)

EXAMPLE 32

N-2-(quinuclidinyl)carbonyl-L-valine- L-alanine-L-aspartic acid 5-(1-phenyl-3-trifluoromethyl)pyrazoyloxymethyl ketone Mass spectrum: m/z=665 (M+H)

EXAMPLE 33

N-(3-pyridyl)methoxycarbonyl-L-valine- L-alanine-L-aspartic acid 5-(1-phenyl-3-trifluoromethyl)pyrazolyloxymethyl ketone Mass spectrum: m/z=663 (M+H)

EXAMPLE 34

N-(2-pyridyl)methoxycarbonyl-L-valine- L-alanine-L-aspartic acid 5-(1-phenyl-3-trifluoromethyl)pyrazolyloxymethyl ketone Mass spectrum: m/z=663 (M+H)

EXAMPLE 35

N-Methyl-N-benzylcarbamoyl- L-valine-L-alanine-L-aspartic acid 5-(1-phenyl-3-trifluoromethyl)pyrazolyloxymethyl ketone Mass spectrum: m/z=674 (M+H)

EXAMPLE 36

N-Methyl-N-[2-(4-pyridyl)ethyl]carbamoyl- L-valine-L-alanine-L-aspartic acid 5-(1-phenyl-3-trifluoromethyl)pyrazolyloxymethyl ketone Mass spectrum: m/z=690 (M+H)

EXAMPLE 37

N-(N-Phenylpiperazino)carbonyl-L-valine- L-alanine-L-aspartic acid 5-(1-phenyl-3-trifluoromethyl)pyrazolyloxy methyl ketone Mass spectrum: m/z=716 (M+H)

EXAMPLE 38

N-Benzyloxycarbonyl-L-valyl-L-2-azetidinyl-L-aspartic acid 5-(1-phenyl-3-trifluoromethyl)pyrazoloxymethyl ketone

EXAMPLE 39

N-Benzyloxycarbonyl-L-prolyl-L-valyl-aspartic acid 5-(1-phenyl-3-trifluoromethyl)pyrazoloxymethyl ketone

EXAMPLE 40

N-4-Pyridinylmethyloxycarbonyl-L-valyl-L-prolyl-L-aspartic acid 5-(1-phenyl-3-trifluoromethyl)pyrazoloxymethyl ketone

EXAMPLE 41

N-Benzyloxycarbonyl-L-valyl-L-3,4-dehydropropyl-L-aspartic acid 5-(1-phenyl-3-trifluoromethyl)pyrazoloxymethyl ketone

EXAMPLE 42

1-(Benzyloxycarbonylamino)cyclopropoyl-L-prolyl-L-aspartic acid 5-(1-phenyl-3-trifluoromethyl)pyrazoloxymethyl ketone

EXAMPLE 43

N-(4-N,N-Dimethylaminomethyl)benzoyl-valyl-prolyl-L-aspartic acid 5-(1-phenyl-3-trifluoromethyl)pyrazoloxymethyl ketone

EXAMPLE 44

N-Benzyloxycarbonyl-L-valyl-L-pipecolyl-L-aspartic acid 5-(1-phenyl-3-trifluoromethyl)pyrazoloxymethyl ketone

EXAMPLE 45

N-(4-N-Thiazolinylmethyl)benzoyl-L-valyl- L-pipecolyl-L-aspartic acid 5-(1-phenyl-3-trifluoromethyl)pyrazoloxymethyl ketone

EXAMPLE 46

N-Benzyloxycarbonyl-L-t-butylglycinyl-L-pipecolyl- L-aspartic acid 5-(1-(2-pyridinyl)-3-trifluoromethyl)pyrazoloxymethyl ketone

EXAMPLE 47

N-Benzyloxycarbonyl-L-valyl- D,L-tetrahydroisoquinoyl-L-aspartic acid 5-(1-phenyl-3-trifluoromethyl)pyrazoloxymethyl ketone

EXAMPLE 48

N-(4-Pyridinylmethyl)-L-valyl-N-methylalanyl-L-aspartic acid 1-phenyl-3-trifluoromethyl)pyrazoloxymethyl ketone

EXAMPLE 49

N-Methoxycarbonyl-L-(ε-N-benzyloxycarbonyl) lysinyl-L-alanyl-L-aspartic acid 5-(1-phenyl-3-trifluoromethyl)pyrazoloxymethyl ketone

EXAMPLE 50

N-Methoxycarbonyl-L-lysinyl-L-alanyl-L-aspartic acid 5-(1-phenyl-3-trifluoromethyl)pyrazoloxymethyl ketone

EXAMPLE 51

N-Benzyloxycarbonyl-L-valyl-L-t-butylglycinyl-L-aspartic acid 5-(1-phenyl-3-trifluoromethyl)pyrazoloxymethyl ketone

EXAMPLE 52

N-Benzyloxycarbonyl-L-t-butylglycinyl-L-alanyl-L-aspartic acid 5-(1-phenyl-3-trifluoromethyl)pyrazoloxymethyl ketone

EXAMPLE 53

N-Benzyloxycarbonyl-D-alanyl-L-valyl-L-aspartic acid 5-(1-phenyl-3-trifluoromethyl)pyrazoloxymethyl ketone

EXAMPLE 54

N-(4-N-Pyrollodinylmethyl)benzoyl-L-valyl- L-alanyl-L-aspartic acid 5-(1-phenyl-3-trifluoromethyl)pyrazoloxymethyl ketone

EXAMPLE 55

N-(4-(N-Methylpiperizyl)methyl)benzoyl-L-valyl-L-alanyl-D,L-aspartic acid 5-(1-phenyl-3-trifluoromethyl)pyrazoloxymethyl ketone

EXAMPLE 56

N-(4-(N-Thiazolidinylmethyl)benzoyl-L-valvyl-L-alanyl-aspartic acid 5-(1-phenyl-3-trifluoromethyl)pyrazoloxymethyl ketone

EXAMPLE 57

N-Benzoyl-L-valyl-L-alanyl-L-aspartic acid 5-(1-phenyl-3-trifluoromethyl)pyrazoloxymethyl ketone

EXAMPLE 58

N-(4-N,N-Dimethylaminoethoxy)benzoyl- L-valyl-L-alanyl-L-aspartic acid 5-(1-phenyl-3-trifluoromethyl)pyrazoloxymethyl ketone

EXAMPLE 59

N-4-Thiomethylbenzoyl-L-valyl-L-alanyl-L-aspartic acid 5-(1-phenyl-3-trifluoromethyl)pyrazoloxymethyl ketone

EXAMPLE 60

N-4-(N,N-Diethylaminomethyl)benzoyl-L-valyl-L-alanyl-L-aspartic acid 5-(1-phenyl-3-trifluoromethyl)pyrazoloxymethyl ketone

EXAMPLE 61

N-4-(2,6-Dimethylpyridinyl)methoxycarbonyl-L-valyl-L-alanyl-L-aspartic acid 5-(1-phenyl-3-trifluoromethyl)pyrazoloxymethyl ketone

EXAMPLE 62

N-4-(N-Morpholinylmethyl)benzoyl-L-valyl- L-alanyl-L-aspartic acid 5-(1-phenyl-3-trifluoromethyl)pyrazoloxymethyl ketone

EXAMPLE 63

N-3-(N,N-Dimethylaminomethyl)benzoyl-L-valyl-L-alanyl-L-aspartic acid 5-(1-phenyl-3-trifluoromethyl)pyrazoloxymethyl ketone

EXAMPLE 64

N-3-(1-Naphthyl)propionyl-L-valyl-L-aspartic acid 5-(1-(4-chlorophenyl)-3-trifluoromethyl) pyrazoloxymethyl ketone

EXAMPLE 65

N-3-(4-Quinolinyl)propionyl-L-valyl-L-aspartic acid 5-(1-(4-chlorophenyl)-3-trifluoromethyl) pyrazoloxymethyl ketone

EXAMPLE 66

N-3-(3-Benzothienyl)propionyl-L-valyl-L-aspartic acid 5-(1-(4-chlorophenyl)-3-trifluoromethyl) pyrazoloxymethyl ketone

EXAMPLE 67

N-(4-Methylsulfenyl)benzoyl-L-valyl-L-alanyl-L-aspartic acid 5-(1-phenyl-3-trifluoromethyl)pyrazoloxymethyl ketone

EXAMPLE 68

N-(4-N-Morpholinylethoxy)benzoyl-L-valyl- L-alanyl-L-aspartic acid 5-(1-phenyl-3-trifluoromethyl)pyrazoloxymethyl ketone

EXAMPLE 69

N-(S-2-Hydroxy-3-methyl)propionyl-L-valyl-L-aspartic acid 5-(1-phenyl-3-trifluoromethyl)pyrazoloxymethyl ketone

EXAMPLE 70

N-(3-N-Piperidinyl)propionyl-L-valyl-L-alanyl-L-aspartic acid 5-(1-phenyl-3-trifluoromethyl)pyrazoloxymethyl ketone

EXAMPLE 71

N-(N-Phenyl-piperazinyl)formyl-L-valyl-L-alanyl-L-aspartic acid 5-(1-phenyl-3-trifluoromethyl)pyrazoloxymethyl ketone

EXAMPLE 72

N-(S-1-Hydroxy-2-phenyl)propionyl-L-valyl-L-aspartic acid 5-(1-phenyl-3-trifluoromethyl)pyrazoloxymethyl ketone

EXAMPLE 73

N-Benzyloxycarbonyl-L-valyl-L-aspartic acid 5-(1-(4-(7-chloro)quinolinyl-3-trifluoromethyl) pyrazoloxymethyl ketone

EXAMPLE 74

N-Benzyloxycarbonyl-L-valyl-L-alanyl-L-aspartic acid 5-(1-(4-(7-chloro)quinolinyl-3-trifluoromethyl) pyrazoloxymethyl ketone

EXAMPLE 75

N-Benzyloxycarbonyl-L-valyl-L-alanyl-L-aspartic acid 5-(1-(4-chloro)phenyl-3-trifluoromethyl) pyrazoloxymethyl ketone Ethyl ester

EXAMPLE 76

N-Benzyloxycarbonyl-L-valyl-L-alanyl-L-aspartic acid 5-(1-phenyl-3-trifluoromethyl)pyrazoloxymethyl ketone Ethyl ester

EXAMPLE 77

N-Benzyloxycarbonyl-L-aspartic acid 5-(1-(4-fluorophenyl)-3-methyl)pyrazoloxymethyl ketone Methyl ester

EXAMPLE 78

N-Benzyloxycarbonyl-L-aspartic acid 5-(1-phenyl-3-methyl)pyrazoloxymethyl ketone Benzyl ester

EXAMPLE 79

N-Benzyloxycarbonyl-L-valyl-L-aspartic acid 5-(1-phenyl-3-trifluoromethyl)pyrazoloxymethyl ketone Isopropyl ester

EXAMPLE 80

N-Benzyloxycarbnyl-L-aspartic acid 5-(1-phenyl-3-methyl)pyrazoloxymethyl ketone 2-Aminoethyl ester

EXAMPLE 81

N-Benzyloxycarbonyl-L-aspartic hydroxamic acid 2,6-dichlorobenzoyloxymethyl ketone

EXAMPLE 82

N-(4-(1-Carboxyethyl)benzoyl-L-valyl-L-alanyl-L-aspartic acid 5-(1-phenyl-3-trifluoromethyl)pyrazoloxymethyl ketone

EXAMPLE 83

N-Benzyloxycarbonyl-L-valyl-L-alanyl-L-aspartic acid 5-(1-(5-chloro-2-pyridinyl-3-trifluoromethyl)pyrazoloxymethyl ketone

EXAMPLE 84

N-(1-Naphthyl)ethoxycarbonyl-L-valyl-L-aspartic acid 5-(1-(4-chorophenyl)-3-trifluoromethyl)pyrazoloxymethyl ketone Examples 85–89 represent formula (1) (coumarinoloxymethyl ketones) wherein:

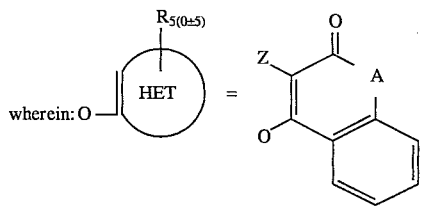

wherein:

A=oxygen or sulfur or N—Z;

Z is defined as H, alkyl, or phenyl where phenyl is defined as a phenyl ring where up to three hydrogen atoms are independently substituted with alkyl, alkoxy, halo or an unsubstituted phenyl ring; and all other substituents are as described above.

The coumarinoloxymethyl ketones of the invention are prepared by reacting the coumarin with an aspartic-acid derived bromomethylketone in DMF in the presence of potassium fluoride. This is followed by treatment with trifluoroacetic acid (TFA) in a chlorinated solvent, for example methylene chloride.

The coumarins are purchased commercially or synthesized by procedures known in the art. See, for example:

General Papers for Preparation of 4-hydroxycoumarins:
1) Van Zanten, B.; Nauta, W. T., "The Effect of Alkyl Substitution in Drugs. Chemical and Pharmacological Properties of Subst. 3-Aryl-4-Hydroxycoumarins", (1973), *Arzn Forschung*, 29–34.
2) Sripathi, S. K.; Gandhidasan, R.; Raman, P. V., "Synthesis of 3-Aryl-4-Hydroxycoumarins". *Indian J. Heterocyclic Chem.* (1992), 1(4), 155–6.
3) Lokhande, P. D.; Ghiya, B. J., "Novel Method in Synthesis of 3-Phenyl-4-Styryl and 3-Phenyl-4-Hydroxycoumarins", *J. Indian Chem. Soc.* (1989), 66 (5), 314–15.
4) Gandhidasan, R.; Neelakantan, S.; Raman, P. V.; Sripathi; S. K., A New One-Step Synthesis of 3-Aryl-4-Hydroxycoumarins", *Indian J. Chem.*, Section B, (1988), 27B(9) 849.
5) Jain, A. C.; Kumar, A.; Ray, P. C., "Aromatic Benzyhydrylation. Part IX. Synthesis of Nuclear Benzhydrylated 4-Methylcoumasins and 4-Hydroxy-3-Phenylcoumarins", *Indian J. Chem.*, Sect. B, (1986), 25B(6), 623–5.
6) Sreenivasulu, B.; Sundaramurthy, V.; Subba Rao, N. V., "Search for Physiologically Active Compounds. XXVI. Synthesis of Amino- and Halo-Subst. 4-Hydroxy-3-Phenylcoumarins and Isoflavones", *Proc. Indian Acad. Sci.*, Sect. A; (1974), 80(6), 273–7.
7) Jain, A. C.; Jain, S. M.; Singh, J. "Synthesis of Robustis and Related 4-Hydroxy-3-Phenylcoumarins and -Isoflavones", *Tetrahedron*. (1974), 30(15), 2485–92.
8) Jain, A. C.; Jain, S. M., "Synthesis Studies in Isopentenylated 4-Hydroxy-3-Phenylcoumarins", *Indian J. Chem.* (1973), 11(2), 106–8.
9) Sripathi, S. K.; Gandhidasan, R.; Raman, P. V., "Synthesis of 3-Aryl-4-Hydroxy-Coumarins", *Indian J. Heterocycl. Chem.* (1992), 1(14), 155–156.
10) Nakazumi, H.; Kitao, T., "Synthesis and Spectral Characteristics of 4-H-1-Benzothiopyran-4-ones". *Bull. Chem. Soc. Jpn.* (1977), 50(4), 939–44.
11) Jamkhand, P. S.; Rajagopal, S., "Synthesis of 4-Hydroxy-1-Thiocoumarins", *Arch. Pharm. Der. Dtsch. Pharm. Ges.*, (1967), 300(6), 561–6.

The following examples will further illustrate the compounds of the present invention.

EXAMPLE 85

N-Benzyloxycarbonyl-L-valine-L-aspartic acid 3-phenylcoumarinoloxymethyl ketone

Part A:

N-Benzyloxycarbonyl-L-valine-L-aspartic acid bromomethyl ketone β-tert butyl ester (1.16) mmol) was dissolved in 2 mL of DMF containing 4-hydroxy-3-phenylcoumarin (Purchased from APIN Chemicals, Ltd., Unit 1, Milton Park, Near Abingdon, Oxon Ox14, 4RS, UK) (1.4 mmol) and powdered anhydrous KF (1.6 mmol). The reaction mixture was stirred under $N_2$ for 16 hrs. The mixture was diluted with water (30 mL), extracted with ether (3×20 mL), and the organic layer was washed with 0.1N NaOH (3×10) mL followed by brine. The ether solution was dried over magnesium sulfate and concentrated in vacuo to afford (85%) of the β-tert butyl ester as a brown solid.

Part B:

The β-tert butyl ester obtained in Part A above (1 mmol) was dissolved in 25% trifluoroacetic acid −75% $CH_2Cl_2$ and the solution was stirred for 2 hrs at 25° C. The solvent was removed in vacuo and the residue was triturated with ether. The white solid was collected and dried to give the title compound in 100% yield. Mass spectrum: m/z 601 (M+), 363, 273, 239.

EXAMPLE 86

N-Benzyloxycarbonyl-L-aspartic acid coumarinoloxymethyl ketone (Anal. Calcd. for $C_{22}H_{19}NO_8$ 0.25 $H_2O$: C (67.47), H (4.50), N (3.26). Found C (61.53), H (4.35), N (3.27)) was prepared as described above from 4-hydroxy-coumarin and N-benzyloxycarbonyl-L-aspartic acid bromomethyl ketone.

EXAMPLE 87

N-Benzyloxycarbonyl-L-aspartic acid thiocoumarinoloxymethyl ketone (Anal. Calcd. for $C_{22}H_{19}NO_7S$ 0.5 $H_2O$: C (58.66), H (4.48), N (3.11). Found C (58.75), H (4.41), N (3.00)) was prepared as described above from 4-hydroxy-thiocoumarin and N-benzyloxycarbonyl-L-aspartic acid bromomethyl ketone.

EXAMPLE 88

N-Benzyloxycarbonyl-L-aspartic acid phenylcoumarinoloxymethyl ketone (Anal. Calcd. for $C_{28}H_{23}NO_8 \cdot H_2O$: C (64.74), H (4.85), N (2.70). Found C (64.77), H (4.82), N (2.79)) was prepared as described above from 4-hydroxy-3-phenylcoumarin and N-benzyloxycarbonyl-L-aspartic acid bromomethyl ketone.

EXAMPLE 89

N-Benzyloxycarbonyl-L-valine-L-alanine-aspartic acid 3-phenylcoumarinoloxymethyl ketone (mass spectrum m/z 672 (M+), 628, 587, 531) was prepared as described above from 4-hydroxy-3-phenylcoumarin and N-benzyloxycarbonyl-L-valine-L-alanine-L-aspartic acid bromomethyl ketone.

Formula 1 is further represented by examples 90–96, (isoxazoloymethyl ketones), wherein

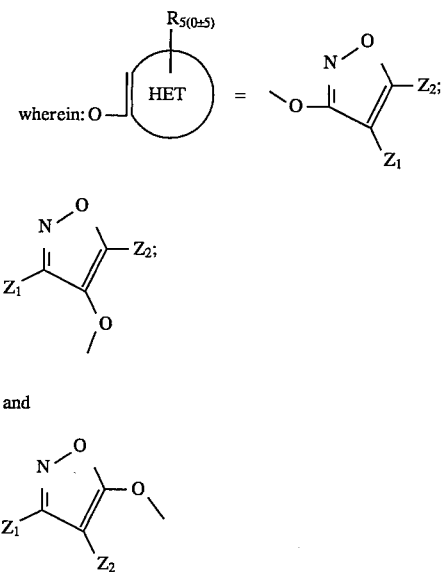

$Z_1$ and $Z_2$ are independently H, alkyl, phenyl or naphthyl, where phenyl and naphthyl are defined as a phenyl or naphthyl ring where up to three hydrogen atoms are independently substituted with alkyl, alkoxy, halo or an unsubstituted phenyl ring and all other substituents are as earlier defined.

The isoxazoloxymethyl ketones of the invention are prepared by reacting the hydroxy isoxazole with an aspartic acid derived bromomethylketone in DMF in the presence of potassium fluoride. This is followed by treatment with trifluoroacetic acid (TFA) in a chlorinated solvent, for example methylene chloride.

The hydroxy isoazoles are purchased commercially or may be synthesized by those skilled in the art using either known procedures or adopting known procedures as described in the literature. See, for example,
Desimoni, G.; et al., *Ann. Chim.* (1968), 58, 1363–1369.
Nakamura, N.; et al., *Heterocycles* (1982) 17, 235–245.
Iwai, I.; et al., *Chem Pharm. Bull., Jpn.* (1966), 14, 1277–1286.
Jacquier, R.; Petrus, C.; et al., *Bull Soc. Chim. Fr.* (1970), 2685–2690.
Jacquier, R.; Petrus, C.; et al., *Bull Soc. Chim. Fr.* (1970), 1978–1985.
Nesi, R.; Giomi, D.; et al., *J. Org. Chem.* (1989), 54, 706–708.
Boyd, G. V.; Norris, T. J., *Chem Soc. Perkin*, Trans (1974), 1, 1028–1030.
Bianchi, G.; Cook, M. J.; Katritzky, A.1 *Tetrahedron*, (1971), 27, 6133–41.
Kiel, G. *Justus Liebigs, Ann. Chem.* (1978), 1540–1542.
Srivartavia, U. K.; Pandey, B. R.; et al., *Pharmazie*, (1979), 34, 14–16.

The following examples will further illustrate the compounds of the present invention.

EXAMPLE 90

N-Benzyloxycarbonyl-L-valine-D,L-aspartic acid 4-(3-phenyl)isoxazoloxymethyl ketone Part A:

N-Benzyloxycarbonyl-L-valine-L-aspartic acid bromomethyl ketone β-tert butyl ester (1.16 mmol) was dissolved in 2 mL of DMF containing 4-hydroxyisoxazole (Desimoni, G. et al) (1.4 mmol) and powdered anhydrous KF (1.6 mmol). The reaction mixture was stirred under $N_2$ for 16 hrs. The mixture was diluted with water (30 mL), extracted with ether (3×20 mL), and the organic layer was washed with 0.1N NaOH (3×10 mL) followed by brine. The ether solution was dried over magnesium sulfate and concentrated in vacuo to afford (85%) of the β-tert-butyl ester (Formula 3) as a brown solid.

Part B:

The β-tert butyl ester obtained in Part A above (1 mmol) was dissolved in 25% trifluoroacetic acid –75% $CH_2Cl_2$ and the solution was stirred for 2 hrs at 25° C. The solvent was removed in vacuo and the residue was triturated with ether. The white solid was collected and dried to give the title compound in 100% yield. Mass spectrum: m/z 533 (M+H).

EXAMPLE 91

N-Benzyloxycarbonyl-L-valine-D,L-aspartic acid 3-(4-phenyl)isoxazoloxymethyl ketone (mass spectrum m/z 524 (M+H)) was prepared similarly from 3-hydroxy-5-methyl-4-phenylisoxazole (Nakamura, N.; et al. supra).

EXAMPLE 92

N-Benzyloxycarbonyl-L-valine-L-alanine-L-aspartic acid 5-(3-phenyl)isoxazoloymethyl (mass spectrum m/z 595 (M+H)) was prepared similarly from 5-hydroxy-3-phenylisoxazole and N-benzyloxycarbonyl-L-valine-L-alanine-L-aspartic acid bromomethyl ketone.

EXAMPLE 93

N-Benzyloxycarbonyl-L-valine-L-alanine-L-aspartic acid 5-[3-(4-pyridinyl)]isoxazoloxymethyl ketone (mass spectrum m/z 596 (M+H)) was prepared similarly from 5-hydroxy-3-(4-pyridinyl)-isoxazole and Z-Val-Ala-Asp-$CH_2Br$.

Formula (1) is further represented by examples 94–96, (tetramoyloxymethyl ketones) wherein:

$$R_{5(0\pm5)} - \text{HET} - O = \text{Aryl} - C(=O) - N-Z \text{ (with O)}$$

wherein:

Z is defined as H, alkyl, and phenyl
where phenyl is defined as a phenyl ring where up to three hydrogen atoms are independently substituted with alkyl, alkoxy, halo or an unsubstituted phenyl ring; and all other substituents are defined above.

The tetramoyloxymethyl ketones of the invention are prepared by reacting the tetramic acid with an aspartic acid derived bromomethylketone in DMF in the presence of potassium fluoride. This is followed by treatment with trifluoroacetic acid (TFA) in a chlorinated solvent, for example methylene chloride.

The tetramic acids are purchased commercially or synthesized by known procedures including known to those skilled uin the art. See, for example:

1) Prep. of 4-amino and hydroxy-3-phenyl-3-pyrolin-2-ones as herbicides. Baasner, B.; Fisher, R.; Lverssen, K.; Santel, H. J.; Schmidt, R. R. (Bayer A. G. FRG) Eur. Pat. Appl. EP415185 A1, 6 Mar. 1991, 47 pp. Application: EP 90-115656, 16 Aug. 1990.
2) Prep. of 1,5-dihydro-4-(N-methylhydroxy(amino)-2H-pyrrol-2-ones as 5-lipoxygenase inhibitors. Flynn, G. A.; Beight, D. W.; (Merrell Dow Phaarmaceuticals Inc., USA) Eur. Pat. Appl. EP 409163 A$_2$ 23 Jan. 1991, 55 pp. Application: EP 90-113677, 17 Jul. 1990.
3) Pyrrolo[3,2-b]pyrroledione pigments for plastic resins. Fuerstenwerth, H. (Bayer Ag, FRG ) Ger. Offen. DE 3525109 A 1, 15 Jan. 1987, 15 pp. Application DE 85-3525109, 13 Jul. 1985.

EXAMPLE 94

N-Benzyloxycarbonyl-L-valine-D,L-aspartic acid 3-phenyltetramoyloymethyl ketone

Z—Val—Asp(OtBu)CH$_2$Br + [3-phenyl-pyrrolone] → ZVal—Asp(OtBu)CH$_2$O—[Ph-substituted ring]—NH Part A:

A solution of ZVal-Asp(OtBu)CH$_2$Br (0.333 g, 0.68 mmol), 1,5-dihydro-2H-3-phenyl-pyrrol-2-one (100 mg, 0.68 mmol) and, KF (82 mg, 1.7 mmol) in 2.5 mL DMF was stirred overnight at room temperature. The solution was then diluted with water and extracted 4× with EtOAc. The organic layer was then washed with water (1×), sat. NaHCO$_3$ (3×), water (1×) and brine (1×), and dried over Na$_2$SO$_4$. Filtration and concentration provided a light yellow solid. Recrystallization from EtC)Ac/hex provided the coupled product as a fine white solid (190 mg, 48%).

M.P.=119°–121° C.

ZVal—Asp(OtBu)CH$_2$O—[Ph ring with O]—NH → ZVal—AspCH$_2$O—[Ph ring with O]—NH

Part B:

A solution of 25% trifluoroacetic acid/dichloromethane (containing 3 drops H$_2$O was added to a flask containing tBu ester (150 mg, 0.26 mmol; Part A above under N$_2$. The solution was stirred for two hours at room temperature. All solvents and reagents were evaporated under reduced pressure. Toluene (20 mL×3) was added and evaporated. Further evaporation of product from methylene chloride produced a tan solid. Trituration with ether provided the acid as a light tan solid (136 mg, 0.25 mmol) MP 147°–149° C.

EXAMPLE 95

N-Benzyloxycarbonyl-L-valine-D,L-aspartic acid 3-phenyl-N-methyltetramoyloxymethyl ketone (mass spectrum m/z 553 (M+H)) was prepared as described above from 1,5-dihydro-2H-3-phenyl-N-methyl-pyrrol-2-one.

EXAMPLE 96

N-Benzyloxycarbonyl-L-valine-D,L-aspartic acid 3-phenyl-N-phenyltetramoyloxymethyl ketone (mass spectrum m/z 615 (M+H)) was prepared as described above from 1,5-dihydro-2H-3-phenyl-N-phenyl-pyrrol-2-one.

What is claimed is:

1. A compound of the formula for inhibiting interleukin-1β protease activity:

$$R_1-(AA)_n-N(H)-C(H)(CH_2-C(=O)-OH)-C(=O)-CH_2-O-[\text{pyrazole ring with } R_{10}, R_9, R_8, N]$$

or a pharmaceutically acceptable salt thereof, wherein
n is 0–2;
AA is independently L-valine or L-alanine;
R$_1$ is selected from the group consisting of
  N-[4-(N,N-dimethylaminomethyl)]benzoyl,
  N-benzyloxycarbonyl,
  N-methyl-N-[4-(pyridyl)methyl],
  N-[4-(pyridyl)methyl]carbonyl,
  N-3-(piperidinopropionyl),
  N-[4-(morpholinoethoxy)benzoyl,
  N-2-(quinuclidinyl)carbonyl,
  N-(3-pyridyl)methoxy carbonyl,
  N-(2-pyridyl)methoxy carbonyl,
  N-methyl-N-benzyl carbonyl,
  N-methyl-N-[2-(4-pyridyl)ethyl]carbonyl, and
  N-(N-phenylpiperazino)carbonyl; and $R_8$, $R_9$ and $R_{10}$ are each independently hydrogen, lower alkyl, halo substituted methyl, carbalkoxy, benzyl, phenyl, or phenyl mono or disubstituted with fluoro, nitro, methoxy, chloro, trifluoromethyl or methanesulfonyl.

2. The compound according to claim 1 selected from the group consisting of: N-[4-(N,N-Dimethylaminomethyl)]benzoyl-L-valine-L-aspartic acid 5-(1-phenyl-3-trifluoromethyl)pyrazoyloxymethyl ketone, N-Benzyloxycarbonyl-L-aspartic acid 5-(1,3-dimethyl)pyrazolyloxymethyl ketone, N-Benzyloxycarbonyl-L-aspartic acid 5-(1-phenyl-3-trifluoromethyl)pyrazolyloxymethyl ketone, N-Benzyloxycarbonyl-L-aspartic acid 5-(1-(p-fluorophethyl)-3-methyl)pyrazoloyloxy methyl ketone, N-Benzloxycarbonyl-L-aspartic acid 5-(1-(p-nitrophenyl)-3-methyl)pyrazolyloxylmethyl ketone and N-Benzyloxycarbonyl-L-aspartic acid 5-(1(p-methoxyphenyl)-3-methyl)pyrazolyloxymethyl ketone.

3. The compound according to claim 1 selected from the group consisting of: N-Benzyloxycarbonyl-L-aspartic acid 5-(1-(p-chlorophenyl)-3-methyl)pyrazolyloxymethyl ketone, N-Benzyloxycarbonyl-L-valine-L-alanine-L-aspartic acid 5-(1-phenyl-3-methyl)pyrazolyloxymethyl ketone, N-Benzyloxycarbonyl-L-aspartic acid 5-(1-phenyl-3-methyl)pyrazolyloxymethyl ketone, N-Benzyloxycarbonyl-L-aspartic acid 5-(1-(m-chlorophenyl)-3-methyl)pyrazolyloxymethyl ketone, N-Benzyloxycarbonyl-L-aspartic acid 5-(1-benzyl-3-trifluoromethyl)pyrazolyloxymethyl ketone and N-Benzyloxycarbonyl-L-valine-L-alanine-L-aspartic acid 5-(1-phenyl-3-trifluoromethyl)pyrazolyloxymethyl ketone.

4. The compound according to claim 1 selected from the group consisting of: N-Benzyloxycarbonyl-L-aspartic acid 5-(1-(m,p-dichlorophenyl)-3-methyl)pyrazolyloxy methyl ketone, N-Benzyloxycarbonyl-L-valine-L-aspartic acid 5-(1-phenyl-3-trifluoromethyl)pyrazolyloxymethyl ketone, N-Benzyloxycarbonyl-L-valine-L-aspartic acid 5-(1-phenyl-3-methyl)pyrazolyloxy methyl ketone, and N-Benzyloxycarbonyl-L-valine-L-aspartic acid 5-(1-phenyl-3-t-butyl)pyrazolyloxymethyl ketone.

5. The compound according to claim 1 selected from the group consisting of: N-Benzyloxycarbonyl-L-valine-L-aspartic acid 5-(1-(p-trifluoromethylphenyl)-3-methyl)pyrazolyloxymethyl ketone, N-Benzyloxycarbonyl-L-aspartic acid 5-(1-(p-methanesulfonylphenyl)-3-trifluoromethyl)pyrazolyloxymethyl ketone, N-4-(N,N-Dimethylaminomethyl)benzoyl-L-valine-L-alanine-L-aspartic acid 5-(1-phenyl-3-trifluoromethyl)pyrazolyloxymethyl ketone, N-Benzyloxycarbonyl-L-aspartic acid 5-(1,3-dimethyl-4-phenyl)pyrazolyloxymethyl ketone, N-Benzyloxycarbonyl-L-valine-L-aspartic acid 5-(1-(p-methanesulfonylphenyl)-3-methyl)pyrazolyloxymethyl ketone, and N-Benzyloxycarbonyl-L-valine-L-aspartic acid 5-(1,3-dimethyl)-4-phenyl)pyrazolyloxymethyl ketone.

6. The compound according to claim 1 selected from the group consisting of: N-Benzyloxycarbonyl-L-valine-L-aspartic acid 5-(1-phenyl-3-carbethoxy)pyrazolyloxymethyl ketone, N-Benzyloxycarbonyl-L-valine-L-aspartic acid 5-(1,3-diphenyl)pyrazolyloxymethyl ketone, N-Methyl-N-[4-(pyridyl)methyl]carbamoyl-L-valine-L-alanine-L-aspartic acid 5-(1-phenyl-3-trifluoromethyl)pyrazolyloxymethyl ketone, N-[4-(Pyridyl)methyl]carbamoyl-L-valine-L-alanine-L-aspartic acid 5-(1-phenyl-3-trifluoromethyl)pyrazolyloxymethyl ketone, N-Benzyloxycarbonyl-L-valine-L-alanine-D-aspartic acid 5-(1-phenyl-3-trifluoromethyl)pyrazolyloxymethyl ketone and N-Benzyloxycarbonyl-L-valine-L-aspartic acid 5-(1-p-chlorophenyl-3-methyl-4-phenyl)pyrazolyloxymethyl ketone.

7. The compound according to claim 1 selected from the group consisting of: N-Benzyloxycarbonyl-L-valine-L-aspartic acid 5-(1,4-diphenyl-3-methyl)pyrazolyloxymethyl ketone, N-3-(piperidinopropionyl)-L-valine-L-alanine-L-aspartic acid 5-(1-phenyl-3-methyl)pyrazolyloxymethyl ketone, N-[4-(morpholinoethoxy)benzoyl)-L-valine-L-alanine-L-aspartic acid 5-(1-phenyl-3-trifluoromethyl)pyrazolyloxymethyl ketone, N-2-(quinuclidinyl)carbonyl-L-valine-L-alanine-L-aspartic acid 5-(1-phenyl-3-trifluoromethyl)pyrazolyloxymethyl ketone, N-(3-pyridyl)methoxycarbonyl-L-valine-L-alanine-L-aspartic acid 5-(1-phenyl-3-trifluoromethyl)pyrazolyloxymethyl ketone and N-(2-pyridyl)methoxycarbonyl-L-valine-L-alanine-L-aspartic acid 5-(1-phenyl-3-trifluoromethyl)pyrazolyloxymethyl ketone.

8. The compound according to claim 1 selected from the group consisting of: N-Methyl-N-benzylcarbamoyl-L-valine-L-alanine-L-aspartic acid 5-(1-phenyl-3-trifluoromethyl) pyrazolyloxymethyl ketone, N-Methyl-N-[2-(4-pyridyl) ethyl]carbamoyl-L-valine-L-alanine-L-aspartic acid 5-(1-phenyl-3-trifluoromethyl)pyrazolyloxymethyl ketone and N-(N-Phenylpiperazino)carbonyl-L-valine-L-alanine-L-aspartic acid 5-(1-phenyl-3-trifluoromethyl)pyrazolyloxy methyl ketone.

9. A pharmaceutical composition for inhibiting interleukin-1β protease activity comprising an effective inhibitory amount of a compound of the formula:

$$R_1-(AA)_n-\underset{\underset{H}{|}}{\overset{\overset{H}{|}}{N}}-\underset{\underset{O}{\|}}{\overset{\overset{CH_2-\overset{O}{\overset{\|}{C}}-OH}{|}}{C}}-CH_2-O-\underset{\underset{R_8}{|}}{\overset{R_{10}}{\diagup}}\diagdown\underset{N}{\diagdown}\overset{R_9}{\diagup}N$$

or a pharmaceutically acceptable salt thereof, wherein
n is 0–2;
AA is independently L-valine or L-alanine;
$R_1$ is selected from the group consisting of
  N-[4-(N,N-dimethylaminomethyl)]benzoyl,
  N-benzyloxycarbonyl,
  N-methyl-N-[4-(pyridyl)methyl],
  N-[4-(pyridyl)methyl]carbonyl,
  N-3-(piperidinopropionyl),
  N-[4-(morpholinoethoxy)benzoyl,
  N-2-(quinuclidinyl)carbonyl,
  N-(3-pyridyl)methoxy carbonyl,
  N-(2-pyridyl)methoxy carbonyl,
  N-methyl-N-benzyl carbonyl,
  N-methyl-N-[2-(4-pyridyl)ethyl]carbonyl, and
  N-(N-phenylpiperazino)carbonyl; and $R_8$, $R_9$ and $R_{10}$ are each independently hydrogen, lower alkyl, halo substituted methyl, carbalkoxy, benzyl, phenyl, or phenyl mono or disubstituted with fluoro, nitro, methoxy, chloro, trifluoromethyl or methanesulfonyl, in a pharmaceutically acceptable carrier.

10. The pharmaceutical composition of claim 9 wherein said compound is selected from the group consisting of: N-[4-(N,N-Dimethylaminomethyl)]benzoyl-L-valine-L-aspartic acid 5-(1-phenyl-3-trifluoromethyl)pyrazoyloxymethyl ketone, N-Benzyloxycarbonyl-L-aspartic acid 5-(1,3-dimethyl)pyrazolyloxymethyl ketone, N-Benzyloxycarbonyl-L-aspartic acid 5-(1-phenyl-3-trifluoromethyl)pyrazolyloxymethyl ketone, N-Benzyloxycarbonyl-L-aspartic acid 5-(1-(p-fluorophenyl)-3-methyl)pyrazolyloxy methyl ketone, N-Benzyloxycarbonyl-L-aspartic acid 5-(1-(p-nitrophenyl)-3-methyl)pyrazolyloxymethyl ketone and N-Benzyloxycarbonyl-L-aspartic acid 5-(1-(p-methoxyphenyl)-3-methyl)pyrazolyloxymethyl ketone.

11. The pharmaceutical composition of claim 9 wherein said compound is selected from the group consisting of: N-Benzyloxycarbonyl-L-aspartic acid 5-(1-(p-chlorophenyl)-3-methyl)pyrazolyloxymethyl ketone, N-Benzyloxycarbonyl-L-valine-L-alanine-L-aspartic acid 5-(1-phenyl-3-methyl)pyrazolyloxymethyl ketone, N-Benzyloxycarbonyl-L-aspartic acid 5-(1-phenyl-3-methyl)pyrazolyloxymethyl ketone, N-Benzyloxycarbonyl-L-aspartic acid 5-(1-(m-chlorophenyl)-3-methyl)pyrazolyloxymethyl ketone, N-Benzyloxycarbonyl-L-aspartic acid 5-(1-benzyl-3-trifluoromethyl)pyrazolyloxymethyl ketone and N-Benzyloxycarbonyl-L-valine-L-alanine-L-aspartic acid 5-(1-phenyl-3-trifluoromethyl)pyrazolyloxy-methyl ketone.

12. The pharmaceutical composition of claim 9 wherein said compound is selected from the group consisting of: N-Benzyloxycarbonyl-L-aspartic acid 5-(1-(m,p-dichlorophenyl)-3-methyl)pyrazolyloxy methyl ketone, N-Benzyloxycarbonyl-L-valine-L-aspartic acid 5-(1-phenyl-3-trifluoromethyl)pyrazolyloxymethyl ketone, N-Benzyloxycarbonyl-L-valine-L-aspartic acid 5-(1-phenyl-3-methyl)pyrazolyloxy methyl ketone, and N-Benzyloxycarbonyl-L-valine-L-aspartic acid 5-(1-phenyl-3-t-butyl)pyrazolyloxymethyl ketone.

13. The pharmaceutical composition of claim 9 wherein said compound is selected from the group consisting of: N-Benzyloxycarbonyl-L-valine-L-aspartic acid 5-(1-(p-trifluoromethylphenyl)-3-methyl)pyrazolyloxymethyl ketone, N-Benzyloxycarbonyl-L-aspartic acid 5-(1-(p-methanesulfonylphenyl)-3-trifluoromethyl)pyrazolyloxymethyl ketone, N-4-(N,N-Dimethylaminomethyl)benzoyl-L-valine-L-alanine-L-aspartic acid 5-(1-phenyl-3-trifluoromethyl)pyrazolyloxymethyl ketone, N-Benzyloxycarbonyl-L-aspartic acid 5-(1,3-dimethyl-4-phenyl)pyrazolyloxymethyl ketone, N-Benzyloxycarbonyl-L-valine-L-aspartic acid 5-(1-(p-methanesulfonylphenyl)-3-methyl)pyrazolyloxymethyl ketone, and N-Benzyloxycarbonyl-L-valine-L-aspartic acid 5-(1,3-dimethyl)-4-phenyl)pyrazolyloxymethyl ketone.

14. The pharmaceutical composition of claim 9 wherein said compound is selected from the group consisting of: N-Benzyloxycarbonyl-L-valine-L-aspartic acid 5-(1-phenyl-3-carbethoxy)-pyrazolyloxymethyl ketone, N-Benzyloxycarbonyl-L-valine-L-aspartic acid 5-(1,3-diphenyl)pyrazolyloxymethyl ketone, N-Methyl-N-[4-(pyridyl)methyl]carbamoyl-L-valine-L-alanine-L-aspartic acid 5-(1-phenyl-3-trifluoromethyl)pyrazolyloxymethyl ketone, N-[4-(Pyridyl)methyl]carbamoyl-L-valine-L-alanine-L-aspartic acid 5-(1-phenyl-3-trifluoromethyl)pyrazolyloxy-methyl ketone, N-Benzyloxycarbonyl-L-valine-L-alinine-L-aspartic-D-aspartic acid 5-(1-phenyl-3-trifluoromethyl)pyrazolyloxymethyl ketone and N-Benzyloxycarbonyl-L-valine-L-aspartic acid 5-(1-p-chlorophenyl-3-methyl-4-phenyl)pyrazolyloxy-methyl ketone.

15. The pharmaceutical composition of claim 9 wherein said compound is selected from the group consisting of: N-Benzyloxycarbonyl-L-valine-L-aspartic acid 5-(1,4-diphenyl-3-methyl)pyrazolyloxymethyl ketone, N-3-(piperidinopropionyl)-L-valine-L-alanine-L-aspartic acid 5-(1-phenyl-3methyl)pyrazolyloxymethyl ketone, N-[4-(morpholinoethoxy)benzoyl]-L-valine-L-alanine-L-aspartic 5-(1-phenyl-3-trifluoromethyl)pyrazolyloxymethyl ketone, N-2-(quinuclidinyl)carbonyl-L-valine-L-alanine-L-aspartic acid 5-(1-phenyl-3-trifluoromethyl)pyrazolyloxymethyl ketone, N-(3-pyridyl)methoxycarbonyl-L-valine-L-alanine-L-aspartic acid 5-(1-phenyl-3-trifluoromethyl)pyrazolyloxymethyl ketone and N-(2-pyridyl) methoxycarbonyl-L-valine-L-alanine-L-aspartic acid 5-(1-phenyl-3-trifluoromethyl)pyrazolyloxymethyl ketone.

16. The pharmaceutical composition of claim 9 wherein said compound is selected from the group consisting of: N-Methyl-N-benzylcarbamoyl-L-valine-L-alanine-L-aspartic acid 5-(1-phenyl-3-trifluoromethyl)pyrazolyloxymethyl ketone, N-Methyl-N-[2-(4-pyridyl)ethyl]carbamoyl-L-valine-L-alanine-L-aspartic acid 5-(1-phenyl-3-trifluoromethyl) pyrazolyloxymethyl ketone and N-(N-Phenylpiperazino)carbonyl-L-valine-L-alanine-L-aspartic acid 5-(1-phenyl-3-trifluoromethyl)pyrazolyloxy methyl ketone.

17. A method for inhibiting interleukin-1β protease activity in a mammal in need of such treatment comprising administering to said mammal an effective interleukin-1β protease inhibitory amount of a pharmaceutical composition comprising a compound of the formula:

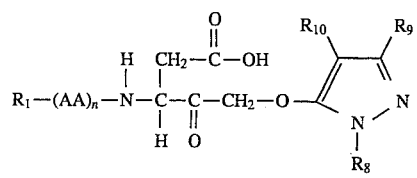

or a pharmaceutically acceptable salt thereof, wherein
n is 0–2;

AA is independently L-valine or L-alanine;
$R_1$ is selected from the group consisting of
N-[4-(N,N-dimethylaminomethyl)]benzoyl,
N-benzyloxycarbonyl,
N-methyl-N-[4-(pyridyl)methyl],
N-[4-(pyridyl)methyl]carbonyl,
N-3-(piperidinopropionyl),
N-[4-(morpholinoethoxy)benzoyl,
N-2-(quinuclidinyl)carbonyl,
N-(3-pyridyl)methoxy carbonyl,
N-(2-pyridyl)methoxy carbonyl,
N-methyl-N-benzylcarbonyl,
N-methyl-N-[2-(4-pyridyl)ethyl]carbonyl, and
N-(N-phenylpiperazino)carbonyl; and $R_8$, $R_9$ and $R_{10}$ are each independently hydrogen, lower alkyl, halo substituted methyl, carbalkoxy, benzyl, phenyl, or phenyl mono or disubstituted with fluoro, nitro, methoxy, chloro, trifluoromethyl or methanesulfonyl, in a pharmaceutically acceptable carrier.

18. The method of claim 17 wherein said compound is selected from the group consisting of: N-[4-(N,N-Dimethylaminomethyl)]benzoyl-L-valine-L-aspartic acid 5-(1-phenyl-3-trifluoromethyl)pyrazoyloxymethyl ketone, N-Benzyloxycarbonyl-L-aspartic acid 5-(1,3-dimethyl)pyrazolyloxymethyl ketone, N-Benzyloxycarbonyl-L-aspartic acid 5-(1-phenyl-3-trifluoromethyl)pyrazolyloxymethyl ketone, N-Benzyloxycarbonyl-L-aspartic acid 5-(1-(p-fluorophenyl)-3-methyl)pyrazolyloxy methyl ketone, N-Benzyloxycarbonyl-L-aspartic acid 5-(1-(p-nitrophenyl)-3-methyl)pyrazolyloxymethyl ketone and N-Benzyloxycarbonyl-L-aspartic acid 5-(1-(p-methoxyphenyl)-3-methyl)pyrazolyloxymethyl ketone.

19. The method of claim 17 wherein said compound is selected from the group consisting of: N-Benzyloxycarbonyl-L-aspartic acid 5-(1-(p-chlorophenyl)-3-methyl)pyrazolyloxymethyl ketone, N-Benzyloxycarbonyl-L-valine-L-alanine-L-aspartic acid 5-(1-phenyl-3-methyl)pyrazolyloxymethyl ketone, N-Benzyloxycarbonyl-L-aspartic acid 5-(1-phenyl-3-methyl)pyrazolyloxymethyl ketone, N-Benzyloxycarbonyl-L-aspartic acid 5-(1-(m-chlorophenyl)-3-methyl)pyrazolyloxymethyl ketone, N-Benzyloxycarbonyl-L-aspartic acid 5-(1-benzyl-3-trifluoromethyl)-pyrazolyloxymethyl ketone and N-Benzyloxycarbonyl-L-valine-L-alanine-L-aspartic acid 5-(1-phenyl-3-trifluoromethyl)pyrazolyloxy-methyl ketone.

20. The method of claim 17 wherein said compound is selected from the group consisting of: N-Benzyloxycarbonyl-L-aspartic acid 5-(1-(m,p-dichlorophenyl)-3-methyl)pyrazolyloxy methyl ketone, N-Benzyloxycarbonyl-L-valine-L-aspartic acid 5-(1-phenyl-3-trifluoromethyl)pyrazolyloxymethyl ketone, N-Benzyloxycarbonyl-L-valine-L-aspartic acid 5-(1-phenyl-3-methyl)pyrazolyloxy methyl ketone, and N-Benzyloxycarbonyl-L-valine-L-aspartic acid 5-(1-phenyl-3-t-butyl)pyrazolyloxymethyl ketone.

21. The method of claim 17 wherein said compound is selected from the group consisting of: N-Benzyloxycarbonyl-L-valine-L-aspartic acid 5-(1-(p-trifluoromethylphenyl)-3-methyl)pyrazolyloxymethyl ketone, N-Benzyloxycarbonyl-L-aspartic acid 5-(1-(p-methanesulfonylphenyl)-3-trifluoromethyl)pyrazolyloxymethyl ketone, N-4-(N,N-Dimethylaminomethyl)benzoyl-L-valine-L-alanine-L-aspartic acid 5-(1-phenyl-3-trifluoromethyl)pyrazolyloxymethyl ketone, N-Benzyloxycarbonyl-L-aspartic acid 5-(1,3-dimethyl-4-phenyl)pyrazolyloxymethyl ketone, N-Benzyloxycarbonyl-L-valine-L-aspartic acid 5-(1-(p-methanesulfonylphenyl)-3-methyl)pyrazolyloxymethyl ketone, and N-Benzyloxycarbonyl-L-valine-L-aspartic acid 5-(1,3-dimethyl)-4-phenyl)pyrazolyloxymethyl ketone.

22. The method of claim 17 wherein said compound is selected from the group consisting of: N-Benzyloxycarbonyl-L-valine-L-aspartic acid 5-(1-phenyl-3-carbethoxy)-pyrazolyloxymethyl ketone, N-Benzyloxycarbonyl-L-valine-L-aspartic acid 5-(1,3-diphenyl)pyrazolyloxymethyl ketone, N-Methyl-N[4-(pyridyl)methyl]carbamoyl-L-valine-L-alanine-L-aspartic acid 5-(1-phenyl-3-trifluoromethyl)pyrazolyloxymethyl ketone, N-[4-(Pyridyl)methyl]carbamoyl-L-valine-L-alanine-L-aspartic acid 5-(1-phenyl-3-trifluoromethyl)pyrazolyloxymethyl ketone, N-Benzyloxycarbonyl-L-valine-L-alanine-D-aspartic acid 5-(1-phenyl-3-trifluoromethyl)pyrazolyloxymethyl ketone and N-Benzyloxycarbonyl-L-valine-L-aspartic acid 5-(1-p-chlorophenyl-3-methyl-4-phenyl)pyrazolyloxymethyl ketone.

23. The method of claim 17 wherein said compound is selected from the group consisting of: N-Benzyloxycarbonyl-L-valine-L-aspartic acid 5-(1,4-diphenyl-3-methyl)pyrazolyloxymethyl ketone, N-3-(piperidinopropionyl)-L-valine-L-alanine-L-aspartic acid 5-(1-phenyl-3-methyl)pyrazolyloxymethyl ketone, N-[4-(morpholinoethoxy)benzoyl)-L-valine-L-alanine-L-aspartic acid 5-(1-phenyl-3-trifluoromethyl)pyrazolyloxymethyl ketone, N-2-(quinuclidinyl)carbonyl-L-valine-L-alanine-L-aspartic acid 5-(1-phenyl-3-trifluoromethyl)pyrazolyloxymethyl ketone, N-(3-pyridyl)methoxycarbonyl-L-valine-L-alanine-L-aspartic acid 5-(1-phenyl-3-trifluoromethyl)pyrazolyloxymethyl ketone and N-(2-pyridyl)methoxycarbonyl-L-valine-L-alanine-L-aspartic acid 5-(1-phenyl-3-trifluoromethyl)pyrazolyloxymethyl ketone.

24. The method of claim 17 wherein said compound is selected from the group consisting of: N-Methyl-N-benzylcarbamoyl-L-valine-L-alanine-L-aspartic acid 5-(1-phenyl-3-trifluoromethyl)pyrazolyloxymethyl ketone, N-Methyl-N-[2-(4-pyridyl)ethyl]carbamoyl-L-valine-L-alanine-L-aspartic acid 5-(1-phenyl-3-trifluoromethyl)pyrazolyloxymethyl ketone and N-(N-Phenylpiperazino)carbonyl-L-valine-L-alanine-L-aspartic acid 5-(1-phenyl-3-trifluoromethyl)pyrazolyloxy methyl ketone.

* * * * *